United States Patent [19]

Schneider et al.

[11] Patent Number: 5,403,962
[45] Date of Patent: Apr. 4, 1995

[54] CHROMIUM-FREE CATALYST FOR THE HYDROGENATION OF ORGANIC COMPOUNDS

[75] Inventors: Michael Schneider, Ottobrunn; Karl Kochloefl, Bruckmuhl/Heufeld; Gerd Maletz, Bruckmühl, all of Germany

[73] Assignee: Sud-Chemie AG, Germany

[21] Appl. No.: 251,625

[22] Filed: May 31, 1994

Related U.S. Application Data

[63] Continuation of Ser. No. 986,104, Dec. 4, 1992, abandoned.

[30] Foreign Application Priority Data

Dec. 13, 1991 [DE] Germany .............. 41 41 199.4

[51] Int. Cl.$^6$ .............. C07C 29/141; C07C 29/145; C07C 29/149; C07C 31/125
[52] U.S. Cl. .............. 568/885; 502/241; 502/324; 568/862; 568/864; 568/881
[58] Field of Search .............. 568/885, 881, 862, 864

[56] References Cited

U.S. PATENT DOCUMENTS

| | | | |
|---|---|---|---|
| 2,061,470 | 11/1936 | Larson | 502/241 X |
| 2,322,096 | 6/1943 | Schmidt | 568/885 |
| 2,322,097 | 6/1943 | Schmidt | 568/885 |
| 3,197,418 | 7/1965 | Maebashi et al. | 568/885 X |
| 3,787,332 | 1/1974 | Sugier | 502/324 X |
| 3,899,577 | 8/1975 | Sugier | 423/656 |
| 4,324,695 | 4/1982 | Hinnenkamp | 568/883 |
| 4,559,316 | 12/1985 | Mazanec et al. | 502/73 |
| 4,611,085 | 9/1986 | Kitson | 568/885 |
| 5,008,235 | 4/1991 | Wegman | 502/342 |

FOREIGN PATENT DOCUMENTS

| | | |
|---|---|---|
| 300346 | 7/1988 | European Pat. Off. . |
| 434062 | 6/1991 | European Pat. Off. . |
| 1248623 | 8/1967 | Germany . |
| 034338 | 2/1981 | Germany . |
| 4021230 | 1/1991 | Germany . |
| 0749069 | 5/1956 | United Kingdom ............ 568/885 |
| 2025252 | 1/1980 | United Kingdom . |
| 399097 | 1/1974 | U.S.S.R. . |

*Primary Examiner*—Joseph E. Evans
*Attorney, Agent, or Firm*—Scott R. Cox

[57] ABSTRACT

The invention describes a chromium-free catalyst for hydrogenation of organic compounds, especially organic compounds containing the carbonyl function, such as aldehydes, ketones, or carboxylic acids or their esters, to the corresponding alcohols wherein the catalysts is characterized by the following features:
its oxide form corresponds to the composition $$Cu_aAl_bZr_cMn_dO_x$$

wherein the following relations apply:
for the first embodiment:
$a>0$; $b>0$; $c\geq 0$; $d>0$; $a>b/2$; $b>a/4$; $a>c$; $a>d$;
and for the second embodiment:
$a>0$; $b=a/40$ to $a/4$; $c\geq 0$; $d>0$; $a>c$; $a=0.5$ d to 0.95 d
and x is the number of oxygen ions needed per formula unit for electrical neutrality.

6 Claims, No Drawings

CHROMIUM-FREE CATALYST FOR THE HYDROGENATION OF ORGANIC COMPOUNDS

This is a continuation of application Ser. No. 07/986,104, filed on Dec. 4, 1992, now abandoned.

BACKGROUND OF THE INVENTION

The field of art to which this invention pertains is catalysts for the hydrogenation of organic compounds.

Fatty alcohols, i.e., aliphatic, predominantly linear, primary alcohols with chain lengths of more than 8 carbon atoms, are important intermediates in the chemical industry. They are used by preference to produce tensides such as fatty alcohol sulfates, polyglycol ethers or polyglycol ether sulfates.

Fatty acids or fatty acid esters, such as the mixture of different chain lengths found in natural fats and oils, are important raw materials for the production of fatty alcohols. They are converted to fatty alcohols by catalytic hydrogenation under pressure, wherein copper-chromium catalysts have proven to be particularly effective.

The hydrogenation reaction is carried out as a suspension hydrogenation, as a gas phase hydrogenation, or in the trickling [liquid] phase. Sufficiently high reaction rates are reached only at pressures about 250 bar and temperatures in the range of 260° to 300° C. As a general rule, the triglycerides are transesterified with methanol by known methods before the hydrogenation, and free fatty acids are esterified. Nevertheless, the reaction mixture has a residual concentration of free carboxylic acids.

The esterifying suspension hydrogenation by the Lurgi process is one important industrial example. In this process, the fatty acid mixture is introduced continuously into the hydrogenation reactor and esterified in situ with the fatty alcohol which is present in excess.

The presence of the free fatty acids obviously places high demands on the resistance of the catalysts to oxygen. Attack by the acids can wash out the catalyst metals, particularly copper, so that the effectiveness of the catalyst is degraded. Furthermore, the product is contaminated by metal soaps, or copper-containing materials deposit in the subsequent parts of the plant.

The Cu—Cr oxide catalysts currently used have satisfactory hydrogenation activity and adequate resistance to the fatty acids in the reaction mixture. One major disadvantage of these catalysts, though, is their chemical composition. Like all catalysts, they lose their activity with time and must be disposed of. Used chromium-containing catalysts are considered environmentally hazardous substances, especially since a content of hexavalent chromium cannot be ruled out. Disposal is an increasing problem for operators of fatty alcohol plants, and the costs of disposal affect the economy of the process.

Also, in hydrogenation of aldehydes and ketones a certain content of acidic components can impair the catalyst properties.

Catalysts for hydrogenation of oxygen-containing compounds such as carboxylic acid esters in the vapor phase are known from EP A-0434062. Their major components are copper oxide and aluminum oxide, along with zirconium oxide. The oxide precursors of these catalysts are calcined at not more than 500° C., so that their acid resistance is low. The activity of the catalysts is also relatively low.

A catalyst for reaction of carbon oxides with water vapor is known from SU-A-39 90 97. It contains copper oxide, zinc oxide and aluminum oxide. No zinc oxide is needed for catalysts used in hydrogenation of higher organic compounds which contain the carbonyl function.

A catalyst based on copper oxide and oxides of trivalent metals for reaction of carbon monoxide with hydrogen is known from SU A-38 22 61. Possible trivalent metals are aluminum, chromium, manganese and iron. Chromium is an essential component of these catalysts.

A process for production of hydrogen by reaction of carbon monoxide or carbon monoxide-containing gases with hydrogen at elevated temperatures is known from German B-1 248 623. The process employs catalysts based on copper oxide, aluminum oxide and/or chromium oxide and/or manganese oxide. In all the examples, the catalysts contain chromium oxide. The process has no points in common with the process for which the catalysts of this invention are to be used.

A procedure for producing an oxidation catalyst is known from DD A-242 183. The catalyst precursor is made from copper nitrate, manganese nitrate and aluminum nitrate by precipitation with aqueous sodium carbonate solution. The precursor is washed, dried, and ignited. The aluminum oxide content of these catalysts is greater than 70% by weight.

Hydrogenation catalysts based on copper, aluminum, and a metal from the group consisting of magnesium, zinc, titanium, zirconium, tin, nickel, cobalt, or mixtures of them are known from EP A-0 434062. The catalysts contain no manganese.

A process for production of alcohols using copper-zirconium oxide catalysts is known from German A-4 021 230. These catalysts contain no manganese or aluminum.

Copper-manganese catalysts for hydrogenation of fatty acids, fatty acid glyceride esters or the lower alkyl esters of fatty acids to fatty alcohols of corresponding chain length are known from German A-4 028 295. These catalysts contain no aluminum.

The objective of the present invention is to obtain catalysts having high hydrogenating activity, good resistance to acidic components and, at the same time, no environmentally damaging effect. Such catalysts are to be used for hydrogenating organic compounds, particularly compounds containing the carbonyl function, such as aldehydes, ketones, or carboxylic acids or their esters.

SUMMARY OF THE INVENTION

This invention is directed to chromium-free catalysts used in the hydrogenation of organic compounds.

The catalyst of this invention in the oxide form has the chemical composition which corresponds to the formula $$Cu_a Al_b Zr_c Mn_d O_x$$

wherein in the first embodiment, the following relationships hold:
$a>0$; $b>0$; $c\geq 0$; $d>0$; $a>b/2$; $b>a/4$; $a>c$; $a>d$; and x is the number of oxygen ions required per formula unit for electrical neutrality.

In the second embodiment, the following relationship exists:

a>o; b=a/40 to a/4; c>o; d>o; a>c; a=0.5 d to 0.95 d; and x is the number of oxygen ions required per formula unit for electrical neutrality.

DESCRIPTION OF THE INVENTION

The catalyst of this invention in the oxide form can be represented by the general formula $$Cu_aAl_bZr_cMn_dO_x$$

wherein in a first embodiment, the following relationship holds:

a>o; b>o; c≧o; d>o; a>b/2; b>a/4; a>c; a>d; and x is the number of oxygen ions required per formula unit for electrical neutrality.

The catalyst of this first embodiment has a BET specific surface between about 10 and about 150 m²/g, and preferably, about 25 and about 125 m²/g.

In a second embodiment, the catalyst in the oxide form can be represented by the same general formula as described above wherein the relationship of the components is as follows:

a>o; b=a/40 to a/4; c≧o; d>o; a>c; a=0.5 d to 0.95 d; and x again is the number of oxygen ions required per formula unit for electrical neutrality.

The catalyst of the second embodiment has BET specific surface between about 5 and about 150 m²/g, and preferably, between about 5 and about 100 m²/g.

The mass of metal dissolved during 2 minutes stirring of 10 g of each embodiment of the catalyst in the oxide form in 100 ml of 10% by weight aqueous acetic acid at 20° C. is not more that 400 mg.

The catalysts of this invention can be made by any of the known methods that guarantee sufficiently intense blending of the components for catalytic use. It is preferred to obtain the oxide form of the catalyst by heat treatment of intermediate stages which are convertible to oxides. The intermediate stages are obtained by simultaneous or consecutive precipitation of the catalyst components. These intermediate stages are then converted to the oxide form by heat treatment.

The intermediate stage compounds, i.e., the poorly soluble compounds, are preferably precipitated from solutions containing the corresponding metal ions in the form of their salts. Suitable salts are, for example, the halides, the sulfates and the nitrates. The zirconium component (if present) is preferably used in the form of acidic zirconyl salt solution, but can also be obtained by hydrolysis of ammoniacal zirconyl carbonate solutions.

All the agents that produce such insoluble intermediates as can be converted into the oxides by thermal treatment are suitable as precipitants. The hydroxides and carbonates, as well as basic carbonates, are especially suitable intermediates, so that alkali carbonates or ammonium carbonate are used as particularly preferred precipitants.

Coprecipitation is considered a particularly suitable method for producing the intermediates.

Washing of the precipitate produced is not particularly critical. The catalysts can contain a certain residual alkali content without damaging their activity. In certain cases, an increase in activity is actually observed.

The thermal treatment of the intermediates is important for producing the catalysts according to the invention, especially in the second embodiment. In the first embodiment, the treatment is carried out in the temperature range between about 500° C. and about 1000° C., preferably in the temperature range between about 600° C. and 900° C. The temperature range for the second embodiment is between about 450° C. to about 900° C., preferably about 500° C. to about 800° C., and most preferably, about 500° C. to about 600° C.

If this thermal treatment is done at too low a temperature, the stabilization of the copper oxide in the matrix is not sufficient. Then the Cu component, or even the other metal components of the catalyst, are dissolved out under the influence of the acidic components in the reaction mixture during the hydrogenation reaction, with the negative effects depicted for the activity of the catalyst, as well as for the product, the reactor, and the subsequent parts of the plant.

The thermal treatment can be carried out discontinuously or continuously, e.g., in a rotary kiln. The catalyst can be introduced into commerce in the oxide form or in a pre-reduced form. The pre-reduction is done in a manner which is itself well-known by heating the oxide form of the catalyst in a reducing atmosphere, generally at temperatures of about 150° C. to about 450° C. However, the catalyst can also be reduced in situ under the conditions existing in the hydrogenation, preferably under pressure (e.g., at a hydrogen pressure of about 300 bar).

In the second embodiment of the catalyst of this invention, the catalyst contains a lower proportion of aluminum oxide. In the development of this second embodiment, it was determined that the lifetime of the catalyst is improved when the proportion of aluminum oxide was reduced. The chemistry of this effect has not as yet been explained in all its details, but there are indications that rehydration phenomena play a decisive role. If the proportion of aluminum oxide is reduced, the thermal treatment specified above for the oxide precursor is essential to increase the acid resistance. Reducing the aluminum content generally reduces the BET specific surface.

In both embodiments, it is preferred that the proportion of manganese be higher than that of zirconium, i.e., d>c.

The catalysts of this invention can also contain an inert carrier material, such as SiO₂, TiO₂ and mixtures thereof.

The catalysts of this invention are useful in the hydrogenation of organic compounds. In addition to hydrogenation of unsaturated organic compounds, the catalysts are used especially in the hydrogenation of organic compounds containing the carbonyl function, such as aldehydes, ketones and carboxylic acids and their esters, to the corresponding alcohols. The compounds containing the carbonyl function can otherwise be saturated, or singly or multiply unsaturated, in the chain.

The catalyst of the invention is particularly suited for liquid-phase hydrogenation of carboxylic acids, especially of fatty acids or fatty acid mixtures with 5 to 24 carbon atoms, and/or their esters, mixed with alcohols if necessary, to the corresponding fatty alcohols. In the process the fatty acids or fatty acid mixtures may be esterified in situ with alcohols in the reaction mixture. Alcohols preferred to be present in the reaction mixture are fatty alcohols or mixtures of fatty alcohols with 4 to 25 carbon atoms.

The catalysts are used as powders in liquid-phase hydrogenation. In vapor-phase hydrogenation, and in hydrogenation of the trickling phase (especially of carboxylic acid esters), the catalyst are used as molded pieces, such as in the form of pressed cylinders, tablets, pastilles, cartwheels, rings, stars or extrusions such as solid extrusions, polylobar extrusions, hollow extrusions, and honeycombs.

The invention is explained by means of the following examples. Examples 1 to 4 refer to production of the catalyst in the first embodiment, while Examples 5 to 8 refer to production of the catalyst in the second embodiment. Example 9 refers to the application of the catalysts of the invention.

EXAMPLE 1

484 g $Cu(No_3)_2.3\ H_2O$, 750 g $Al(NO_3)_3.9\ H_2O$, and 100 g $Mn(N)_3)_2.4H_2O$ are dissolved in a final volume of 2 liters with deionized water, and the solution is heated to 60° C. The solution obtained is then pumped into a stirred precipitation tank over a period of one hour. At the same time, a 1.5 molar sodium carbonate solution, also heated to 60° C., is added at a measured rate such that the pH in the precipitation tank is 6.2±0.2. After the precipitation has stopped, the tank is stirred for another hour at 60° C. The precipitate is filtered and the filter cake is washed and dried overnight at 120° C. It is then calcined as follows: it is heated at 2°/minute to 600° C. and left at that temperature for 3 hours. The BET specific surface was determined as 100 $m^2/g$ by the single-point nitrogen sorption method according to DIN 66 132.

EXAMPLE 2

The preparation is done as described in Example 1 up to the drying of the filter cake. The calcination, however, is done as follows: heating at 2°/minute to 800° C. and holding at that temperature for a period of 3 hours. The BET specific surface is 69 $m^2/g$.

EXAMPLE 3

A Cu-Al-Mn-Zr nitrate solution is prepared by dissolving 484 g $Cu(No_3)_2.3\ H_2O$, 750 g $Al(NO_3)_3.9H_2O$, and 123 g of a zirconyl nitrate solution containing 20% $ZrO_2$ to a total volume of 2 liters. The precipitation and workup including calcination at a maximum temperature of 600° C. are done as described in Example 1. The BET specific surface was determined as 116 $m^2/g$.

EXAMPLE 4

The procedure is as described in Example 3 up to the drying of the filter cake, but the calcination is done as follows: heating at 2°/minute to 800° C. and holding at that temperature for a period of 3 hours. The BET specific surface is 65 $m^2/g$.

EXAMPLE 5

A solution of 1933 g $Cu(No_3)_2.3\ H_2O$, 288 g $Al(NO_3)_3.9H_2O$, and 2134 g $Mn(No_3)_2.4\ H_2O$, in 24 liters of deionized water at 30° C. are pumped, over a period of one hour, into a tank containing a solution of 2729 g NaOH in 17 liters of water. After the conclusion of the precipitation, the temperature is raised to 90° C. and the precipitate is aged for 12 hours. The precipitate is separated with a nutsch filter, washed four times by resuspending it in 20 liters of water each time, and dried overnight at 120° C. The calcination is done as follows: the precipitate is heated at 2°/minute to 600° C. and held at that temperature for 3 hours. The BET specific surface was determined as 6 $m^2/g$.

EXAMPLE 6

341 g $Cu(No_3)_2.3\ H_2O$, 34 g $Al(NO_3)_3.9H_2O$, and 377 g $Mn(No_3)_2.4\ H_2O$ are dissolved in deionized water to a final volume of 3 liters, and the solution is heated to 50° C. The solution is pumped into a stirred precipitation tank over a period of one hour. At the same time, a 1.5 molar sodium carbonate solution, also heated to 50° C., is added at a measured rate such that the pH in the precipitation tank is 6.8±0.2. After the conclusion of the precipitation, the tank is stirred for another hour at 50° C. The precipitate is filtered off and the filter cake is washed and dried overnight at 120° C. It is then calcined as follows: it is heated at 2°/minute to 600° C. and left at that temperature for 3 hours. The BET specific surface was determined as 20 $m^2/g$.

EXAMPLE 7

The catalyst is produced as in Example 6, except that 27 g. pyrogenic silica (Cab-O-Sil LM 150) is also suspended in the solution containing the Cu, Al and Mn nitrates. The BET specific surface was determined to be 71 $m^2/g$.

EXAMPLE 8

The catalyst is prepared once more as in Example 6, but with 27 g. pyrogenic $TiO_2$ (P-25, Degussa) added to the solution containing the Cu, Al, and Mn nitrates. The BET specific surface was determined as 27 $m^2/g$.

The solubilities of the individual metal components were determined as follows as a measure of the acid resistance of the catalysts produced:

10 g of the calcined catalyst is stirred for 10 minutes in 100 ml 10% acetic acid at 20° C. and filtered. The filtrate is analyzed for Cu, Mn, Al and, if appropriate Zr.

EXAMPLE 9

The hydrogenating activity of the catalysts in the suspension hydrogenation of fatty acids was determined as follows:

A 500 ml stirred autoclave was charged with 3 g catalyst and 120 g of a commercial fatty alcohol mixture with a mean carbon chain length of 12 to 18 (CONDEA Alfol 1218). After activation of the catalyst at 200° C. and 300 bar hydrogen pressure, the temperature was raised to 300° C. and 20 g lauric acid were added. Samples were taken throughout the reaction time for determination of the saponification number. The conversion was calculated as $$C = 1 - (SN_t/SN_o)$$

where the subscripts t and o indicate the saponification numbers at the beginning and at time t of the reaction. Assuming first-order kinetics, the rate constant k and the half-life $t_{\frac{1}{2}}$ were obtained as $t_{\frac{1}{2}} = \ln 2/k^2$.

A commercial copper chromite catalyst for hydrogenation of fatty acids (Commercial product, G-99B, of the applicant; metal content: 36.5% Cu, 32% Cr, 2.2% Ba, 2.4% Mn) was tested for comparison. The catalyst of Example 39 of European Patent Application 0 434 062 (27% Cu, 12% Al, 61% Zr) was also tested as comparison example B.

The metal solubilities obtained as described are collected in the following table:

| Example | Solubility (mg metal/10 g catalyst) | Hydrogenation activity $t_{\frac{1}{2}}$ |
| --- | --- | --- |
| 1 | 270 | 6.5 |
| 2 | 160 | 6.2 |
| 3 | 280 | 6.7 |
| 4 | 240 | 8.2 |
| 5 | 190 | 5.9 |
| 6 | 130 | 7.5 |
| 7 | 280 | 6.9 |
| 8 | 210 | 7.2 |
| A (comparison) | 300 | 8.5 |
| B (comparison) | 350 | 10.5 |

The results show clearly that the catalysts of the invention are in all cases at least equal to, and even exceed, the comparative commercial catalysts both in their hydrogenation activity and in their resistance to acids. At the same time, they are completely free of environmentally harmful components, in contrast to the catalysts currently being used industrially, so that neither production, their use, or their later disposal endangers humans or the environment.

What is claimed:

1. A process for hydrogenation of organic compounds containing the carbonyl function or unsaturated organic compounds using a chromium-free catalyst which in the oxide form is comprised of a chemical composition corresponding to the formula:

$$Cu_aAl_bZr_cMn_dO_x$$

wherein the following relationships apply:
a>0; b>0; c>0; d>0; a>b/2; b>a/4; a>c; a>d; and x is the number of oxygen ions needed per formula unit for electrical neutrality; wherein after thermal treatment, said catalyst in the oxide form has a BET surface area between about 10 and about 150 m²/g, and wherein the acid resistance of said catalyst as measured by the solubility of the copper, aluminum, zirconium, and manganese in said catalyst in acid is not more than 400 mg as determined by stirring 10 g of said catalyst in 100 ml of 10 weight percent aqueous acetic acid at 20° C. for 2 minutes.

2. The process of claim 1 wherein the organic compounds are aldehydes, ketones, or carboxylic acids or their esters.

3. The process of claim 2 which is a liquid phase hydrogenation of carboxylic acids having 5 to 24 carbon atoms and their esters to the corresponding fatty alcohols.

4. A process for hydrogenation of organic compounds containing the carbonyl function or unsaturated organic compounds which in the oxide form is comprised of a chemical composition corresponding to the formula:

$$Cu_aAl_bZr_cMn_dO_x$$

wherein the following relations apply: a>0; b=a/40 to a/4; c>0; d>70; a>c; a=0.5 d to 0.95 d and x is the number of oxygen ions needed per formula unit for electrical neutrality; wherein after thermal treatment of an intermediate convertible to the oxide in the temperature range from 450° C. to 900° C., said catalyst in the oxide form has a BET surface area between about 10 and about 150 m²/g, and wherein the acid resistance of said catalyst as measured by the solubility of the copper, aluminum, zirconium, and manganese in said catalyst in acid is not more than 400 mg as determined by stirring 10 g of said catalyst in 100 ml of 10 weight percent aqueous acetic acid at 20° C. for 2 minutes.

5. The process of claim 4 wherein the organic compounds are aldehydes, ketones, or carboxylic acids or their esters.

6. The process of claim 5 which is a liquid phase hydrogenation of carboxylic acids having 5 to 24 carbon atoms and their esters to the corresponding fatty alcohols.

* * * * *